United States Patent
Wong et al.

(10) Patent No.: US 9,580,523 B2
(45) Date of Patent: Feb. 28, 2017

(54) PHARMACEUTICAL ELASTOMERIC ARTICLES

(75) Inventors: Wai K. Wong, Wezembeek (BE); Bharat B. Sharma, Karnataka (IN); Bernard D'Cruz, Karnataka (IN)

(73) Assignee: ExxonMobil Chemical Patents Inc., Baytown, TX (US)

(*) Notice: Subject to any disclaimer, the term of this patent is extended or adjusted under 35 U.S.C. 154(b) by 246 days.

(21) Appl. No.: 13/570,920

(22) Filed: Aug. 9, 2012

(65) Prior Publication Data
US 2013/0203865 A1    Aug. 8, 2013

Related U.S. Application Data

(60) Provisional application No. 61/537,230, filed on Sep. 21, 2011.

(51) Int. Cl.

| | |
|---|---|
| *C08F 14/00* | (2006.01) |
| *C08L 23/20* | (2006.01) |
| *C08L 23/22* | (2006.01) |
| *C08F 10/10* | (2006.01) |
| *C08J 3/28* | (2006.01) |
| *C08C 19/26* | (2006.01) |
| *A61L 27/16* | (2006.01) |

(52) U.S. Cl.
CPC .............. *C08F 14/00* (2013.01); *C08L 23/20* (2013.01); *C08L 23/22* (2013.01); *A61L 27/16* (2013.01); *C08C 19/26* (2013.01); *C08F 10/10* (2013.01); *C08J 3/28* (2013.01)

(58) Field of Classification Search
CPC .. A61L 27/16; C08J 3/28; C08C 19/26; C08F 10/10; C08F 14/00; C08L 23/22; C08L 23/20
USPC .................... 522/150, 155, 178; 524/198
See application file for complete search history.

(56) References Cited

U.S. PATENT DOCUMENTS

| | | |
|---|---|---|
| 5,162,445 A | 11/1992 | Powers et al. |
| 5,426,167 A | 6/1995 | Powers et al. |
| 5,459,174 A | 10/1995 | Merrill et al. |
| 5,824,717 A * | 10/1998 | Merrill et al. ............... 522/81 |
| 2005/0148720 A1* | 7/2005 | Li et al. ................... 524/474 |
| 2006/0222681 A1* | 10/2006 | Richard .................... 424/426 |

OTHER PUBLICATIONS

U.S. Appl. No. 61/537,245, filed Sep. 21, 2011, Wong et al.

* cited by examiner

*Primary Examiner* — Michael A Salvitti
(74) *Attorney, Agent, or Firm* — Nancy T. Krawczyk

(57) ABSTRACT

Elastomeric polymers and compounded elastomers having reduced amounts of leachables and improved resistance to γ-irradiation sterilization suitable for pharmaceutical stopper and seal applications. These polymers and compounded elastomers maintain their physical performances upon being exposed to γ-irradiation over time and typical use conditions. The polymer is prepared by reacting a mixture of i) a $C_4$ to $C_7$ isoolefin monomer, ii) a styrene based monomer, and optionally iii) a $C_4$ to $C_{14}$ multiolefin monomer wherein the polymer contains 5 to 15 wt % of styrene derived units.

9 Claims, No Drawings

PHARMACEUTICAL ELASTOMERIC ARTICLES

CROSS REFERENCE TO RELATED APPLICATIONS

This application claims priority to U.S. Provisional Patent Application No. 61/537,230 filed Sep. 21, 2011, the disclosures of which are incorporated herein by reference in its entirety.

FIELD OF THE INVENTION

The present invention is directed to pharmaceutical articles. In particular, the disclosed pharmaceutical articles are comprised of gamma irradiation resistant elastomers.

BACKGROUND OF THE INVENTION

Filled and vulcanized elastomers are widely adopted for pharmaceutical stopper and seal applications. Elastomers have the following desirable properties: sealing and re-sealing performance, ability to be penetrated by needles without resulting in significant fragmentation, and stoppers formed from elastomers retain their physical dimensions upon high temperature sterilization. Other semi-crystalline materials, such as plastics and thermoplastic elastomers, are not able to match the elasticity, needle penetrability and dimension stability performance of amorphous elastomers. The most widely adopted elastomers for parenteral drug packaging today are halobutyl polymers due to their high gas and moisture barrier as well as low level of additives and impurities. The transition in elastomers and elastomer compositions used for the pharmaceutical applications has been driven by many factors, including the need for high cleanliness stoppers that are compatible with modern sensitive drugs, the use of high purity ingredients to minimize any chemical species that migrate out of stopper and interact with medicine (drug compatibility/turbidity), use of low amounts of clean curatives to assure drug stability/compatibility, a tight control on visible and non-visible particle contamination, and the need for low extractables/leachables.

The levels of extractable and leachable of parenteral drug packaging stoppers are being regulated today. In order to achieve good drug compatibility and minimize extractable and leachable, stopper manufacturers generally use raw materials of high cleanliness, optimize formulation to contain least amount of curing agent and other additives, and comply with good manufacturing practices (GMP) or other ISO standards.

High quality pharmaceutical stoppers today are largely made using halobutyl instead of regular butyl due to the versatile curing of the former elastomer. Regular butyl requires high dosage of sulfur and/or zinc containing curing agents and is not acceptable. Bromobutyl elastomer can be cured using low levels of zinc-free and sulfur-free curing agents and therefore, provide a high degree of cleanliness.

Brominated isobutylene para-methylstyrene (BIMSM) elastomer is a very clean elastomer that has been adopted by the industry to make stoppers for packaging expensive drugs such as antibiotics, water for injection, as well as, vaccines and biological products. Unlike halobutyl, BIMSM elastomer has a fully saturated backbone and therefore, does not need butylated hydroxylated toluene (BHT) or other antioxidant and stabilizer such as epoxidized soy bean oil (ESBO) for stabilization. The polymer also contains no oligomer, a by-product of butyl and halobutyl polymerization process. BHT, oligomer and other additives have been found to be extractables that may lead to drug incompatibility with antibiotics and other sensitive drugs. The use of natural rubber is limited due to 'latex sensitivity' issue. The use of other synthetic rubbers are hampered by high gas and moisture permeability, poor oxidation and heat resistance.

Apart from additives and by-products in the elastomer, curing agents adopted for vulcanization are major source of extractables for pharmaceutical stoppers. BIMSM can be cross-linked effectively through the benzylic bromine functional groups and requires less curative than halobutyl for effective crosslinking. Nevertheless any curing agents and processing additives used can potentially be extracted and cause drug incompatibility for sensitive drugs and biological products. Pharmaceutical stoppers also contain filler for mechanical reinforcement.

Additionally, prior to its intended use, pharmaceutical stoppers and seals need to be thoroughly sterilized to rid of all bacteria and micro-organisms. Known methods of sterilization include radiation sterilization and the types of radiation sterilization include electron beam, x-ray, and gamma irradiation. For electron beam radiation, a high energy electron beam accelerator is used to subject the items to relatively high doses of irradiation (higher than for x-ray or gamma). The electron beam has the ability to cause microbial death and render the material sterile to living organisms in the material. This technology is widely used as it is quick, reliable, is an on/off technology and is compatible with most material. In x-ray irradiation, an x-ray machine doses the material with ionizing energy. In gamma irradiation, Cobalt-60 or Cobalt-137 isotopes are used to generate a radiation source, which are then emitted to sterilize the items. This form of irradiation requires shielding for the operators and the emission of rays cannot be turned off as with electron beam and x-ray irradiation.

Despite these known limitations, γ-irradiation sterilization is becoming a common procedure for sterilizing seals and stoppers. Polymers, with unsaturation when subjected to γ-irradiation exposure, exhibit various degrees of crosslinking and chain scissoring at the same time. This will lead to changes in physical performances. Stoppers made using elastomers that are vulnerable to γ-irradiation sterilization will suffer from changes in its hardness, compression set, tear and tensile strength etc., which can subsequently impact stopper performances.

Because of these concerns, the industry is constantly looking to find both elastomers and compounded elastomers having improved resistance to deterioration during sterilization and reduced leachables.

SUMMARY OF THE INVENTION

The present invention is directed to elastomeric polymers and compounded elastomers that have reduced amounts of leachables and improved resistance to γ-irradiation sterilization suitable for pharmaceutical stopper and seal applications. These polymers and compounded elastomers maintain their physical performances upon being exposed to γ-irradiation over time and typical use conditions.

Disclosed herein is a method of producing elastomeric pharmaceutical articles. The method comprising the steps of: a) preparing an elastomeric compound comprising a polymer, b) subjecting the elastomeric compound to gamma irradiation, and c) forming an article with the compound. The polymer is prepared by reacting a mixture of i) a $C_4$ to $C_7$ isoolefin monomer, ii) a styrene based monomer, and optionally iii) a $C_4$ to $C_{14}$ multiolefin monomer wherein the polymer contains 5 to 15 wt % of styrene derived units.

In one aspect of the disclosed method, after subjecting the elastomeric compound to gamma irradiation, the tensile strength of the compound is changed by not more than twenty percent when compared to the tensile strength of the compound prior to the gamma irradiation, i.e., the original tensile strength of the material following cure but prior to any sterilization method. Additionally, and or alternatively, the 100% modulus of the compound is also changed by not more than twenty percent of the 100% modulus of the compound prior to the gamma irradiation.

In another aspect of the disclosed method, when mixing the composition, the polymer is blended with a cure package and at least one filler. The blending preferably takes place under melt mixing conditions.

Also disclosed is an elastomeric pharmaceutical article. The article is comprised of a polymer, the polymer being a random polymer of i) $C_4$ to $C_7$ isoolefin derived units, ii) 5 to 15 wt % para-methylstyrene derived units, and optionally iii) a $C_4$ to $C_{14}$ multiolefin derived units. The article is subjected to at least 25 KGray of gamma irradiation. Following irradiation, the article retains at least 80% of its original tensile strength and 100% modulus.

In one aspect of the disclosed article, the elastomeric pharmaceutical articles are vial stoppers or vial seals.

DETAILED DESCRIPTION OF THE INVENTION

Applicants have determined that certain polymer compounds suitable for pharmaceutical stopper and seal applications offer a greater resistance to γ-irradiation sterilization than conventionally used impermeable elastomers. Styrene containing high barrier polymer compounds maintain their physical performances to a greater degree than conventional high barrier elastomeric polymers upon being exposed to 40 KGray γ-irradiation.

Various specific embodiments, versions and examples of the invention will now be described, including preferred embodiments and definitions that are adopted herein for purposes of understanding the claimed invention.

Polymer may be used to refer to homopolymers, copolymers, interpolymers, terpolymers, etc. Likewise, a copolymer may refer to a polymer comprising at least two monomers, optionally with other monomers. When a polymer is referred to as comprising a monomer, the monomer is present in the polymer in the polymerized form of the monomer or in the derivative form of the monomer. However, for ease of reference the phrase comprising the (respective) monomer or the like is used as shorthand. Likewise, when catalyst components are described as comprising neutral stable forms of the components, it is well understood by one skilled in the art, that the ionic form of the component is the form that reacts with the monomers to produce polymers.

Rubber refers to any polymer or composition of polymers consistent with the ASTM D1566 definition: "a material that is capable of recovering from large deformations, and can be, or already is, modified to a state in which it is essentially insoluble (but can swell) in boiling solvent . . . ". Elastomer is a term that may be used interchangeably with the term rubber.

Elastomeric composition or compounded elastomer refers to any composition comprising at least one elastomer as defined above.

A vulcanized rubber compound by ASTM D1566 definition refers to "a crosslinked elastic material compounded from an elastomer, susceptible to large deformations by a small force capable of rapid, forceful recovery to approximately its original dimensions and shape upon removal of the deforming force". A cured elastomeric composition refers to any elastomeric composition that has undergone a curing process and/or comprises or is produced using an effective amount of a curative or cure package, and is a term used interchangeably with the term vulcanized rubber compound.

The term "phr" is parts per hundred rubber or "parts", and is a measure common in the art wherein components of a composition are measured relative to a total of all of the elastomer components. The total phr or parts for all rubber components, whether one, two, three, or more different rubber components present in a given recipe is always defined as 100 phr. All other non-rubber components are ratioed against the 100 parts of rubber and are expressed in phr. This way one can easily compare, for example, the levels of curatives or filler loadings, etc., between different compositions based on the same relative proportion of rubber without the need to recalculate percents for every component after adjusting levels of only one, or more, component(s).

Isoolefin refers to any olefin monomer having at least one carbon having two substitutions on that carbon.

Multiolefin refers to any monomer having two or more double bonds. In a preferred embodiment, the multiolefin is any monomer comprising two conjugated double bonds such as a conjugated diene like isoprene.

Isobutylene based elastomer or polymer refers to elastomers or polymers comprising at least 70 mol % repeat units from isobutylene.

Alkyl refers to a paraffinic hydrocarbon group which may be derived from an alkane by dropping one or more hydrogens from the formula, such as, for example, a methyl group ($CH_3$), or an ethyl group ($CH_3CH_2$), etc.

Substituted refers to at least one hydrogen group being replaced by at least one substituent selected from, for example, halogen (chlorine, bromine, fluorine, or iodine); alkyl: straight or branched chain having 1 to 20 carbon atoms, which includes methyl, ethyl, propyl, isopropyl, normal butyl, isobutyl, secondary butyl, tertiary butyl, etc.; haloalkyl, which means straight or branched chain alkyl having 1 to 20 carbon atoms which is substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-dibromobutyl, 4,4-difluorobutyl, trichloromethyl, trifluoromethyl, 2,2,2-trifluoroethyl, 2,3,3-trifluoropropyl, 1,1,2,2-tetrafluoroethyl, and 2,2,3,3-tetrafluoropropyl. Thus, for example, a "substituted styrenic unit" includes p-methylstyrene, p-ethylstyrene, etc.

Elastomer

Elastomeric compositions used in the present invention comprise at least one isoolefin based polymer. These polymers are prepared by reacting a mixture of monomers, the mixture having at least (1) a $C_4$ to $C_7$ isoolefin monomer component such as isobutylene, (2) a styrene component, and optionally (3) a multiolefin monomer component. The isoolefin is in a range from 70 to 99.5 wt % of the total monomer mixture in one embodiment, and 85 to 99.5 wt % in another embodiment. The styrene component is present in the monomer mixture from 30 to 3 wt % in one embodiment, 15 to 5 wt % in another embodiment, or 10 to 7.5 wt % in yet another embodiment. When present, the multiolefin component is present in the monomer mixture from 30 to 0.5 wt % in one embodiment, and from 15 to 0.5 wt % in another embodiment. In yet another embodiment, from 8 to 0.5 wt % of the monomer mixture is multiolefin.

The isoolefin is a $C_4$ to $C_7$ compound, non-limiting examples of which are compounds such as isobutylene (also referred to as isobutene), 2-methyl-1-butene, 3-methyl-1-butene, 2-methyl-2-butene, 1-butene, 2-butene, hexene, and 4-methyl-1-pentene. The styrene monomer may be styrene, halostyrene such as dichlorostyrene, alkylstyrene, or haloalkylstyrene. The multiolefin is a $C_4$ to $C_{14}$ multiolefin such as isoprene, butadiene, 2,3-dimethyl-1,3-butadiene, myrcene, 6,6-dimethyl-fulvene, hexadiene, cyclopentadiene, and piperylene.

In one embodiment, the polymer in the composition is a random copolymer comprising a $C_4$ to $C_7$ isomonoolefins, such as isobutylene and an alkylstyrene comonomer, such as para-methylstyrene, containing at least 80%, more alternatively at least 90% by weight of the para-isomer and optionally include functionalized interpolymers wherein at least one or more of the alkyl substituents groups present in the styrene monomer units contain benzylic halogen or some other functional group. In another embodiment, the polymer may be a random elastomeric copolymer of ethylene or a $C_3$ to $C_6$ α-olefin and an alkylstyrene comonomer, such as para-methylstyrene ("PMS") containing at least 80%, alternatively at least 90 wt % of the para-isomer and optionally include functionalized interpolymers wherein at least one or more of the alkyl substituents groups present in the styrene monomer units contain a functional group. Up to 60 mol % of the para-substituted styrene present in the random polymer structure may be functionalized, and in another embodiment from 0.1 to 5 mol %. In yet another embodiment, the amount of functionalized structure is from 0.2 to 3 mol %.

The elastomer used in the invention is preferably functionalized by the substitution on the alkyl substituent group with a halogen. Halogenation typically occurs as a separate step after polymerization of the polymer. Halogenation can be carried out by any means, and the invention is not herein limited by the halogenation process. The halogen wt % is from 0.1 to 10 wt % based in on the weight of the halogenated butyl rubber in one embodiment, and from 0.5 to 5 wt % in another embodiment. In yet another embodiment, the halogen wt % of the halogenated butyl rubber is from 1 to 2.5 wt %.

Alternatively, the functional group on the polymer may be some other functional group which may be incorporated by nucleophilic substitution of either the benzylic halogen or other substitution on the alkyl group pendant to the styrene derived monomer portion of the polymer. Such other functional groups include carboxylic acids; carboxy salts; carboxy esters, amides and imides; hydroxy; alkoxide; phenoxide; thiolate; thioether; xanthate; cyanide; cyanate; amino and mixtures thereof. These functionalized isomonoolefin copolymers, their method of preparation, methods of functionalization, and cure are more particularly disclosed in U.S. Pat. No. 5,162,445.

In an embodiment, the elastomer comprises random polymers of isobutylene and para-methylstyrene containing from 3 to 20 mol % para-methylstyrene wherein up to 60 mol % of the methyl substituent groups present on the benzyl ring contain a bromine or chlorine atom, such as a bromine atom (para-(bromomethylstyrene)), as well as acid or ester functionalized versions thereof.

In another embodiment, the functionality is selected such that it can react or form polar bonds with functional groups present in the matrix polymer, for example, acid, amino or hydroxyl functional groups, when the polymer components are mixed at high temperatures.

In certain embodiments, the random copolymers have a substantially homogeneous compositional distribution such that at least 95 wt % of the polymer has a para-alkylstyrene content within 10% of the average para-alkylstyrene content of the polymer. Exemplary polymers are characterized by a narrow molecular weight distribution (Mw/Mn) of less than 5, alternatively less than 2.5, an exemplary viscosity average molecular weight in the range of from 200,000 up to 2,000,000, and an exemplary number average molecular weight in the range of from 25,000 to 750,000, as determined by gel permeation chromatography.

In an embodiment, brominated poly(isobutylene-co-p-methylstyrene) (BIMSM) polymers generally contain from 0.2 to 5 mol % of bromomethylstyrene groups relative to the total amount of monomer derived units in the copolymer. In another embodiment, the amount of bromomethylstyrene groups is from 0.3 to 2.8 mol % in yet another embodiment, from 0.4 to 2.5 mol % in yet another embodiment and from 0.3 to 2.0 mol % in yet another embodiment, wherein a desirable range may be any combination of any upper limit with any lower limit. Expressed another way, exemplary polymers contain from 0.4 to 6 wt % bromine based on the total weight of the polymer, and from 0.6 to 5.6 wt % per total polymer weight in another embodiment, are substantially free of ring halogen or halogen in the polymer backbone chain.

In one embodiment, the random polymer is a polymer of $C_4$ to $C_7$ isoolefin derived units (or isomonoolefin), para-methylstyrene derived units and para-(halomethylstyrene) derived units, wherein the para-(halomethylstyrene) units are present in the polymer from 0.4 to 3.0 mol % based on the total number of monomers derived units in the polymer, and wherein the para-methylstyrene derived units are present from 3 to 20 wt % based on the total weight of the polymer in one embodiment, and from 5 to 15 wt % in another embodiment. In another embodiment, the para-(halomethylstyrene) is para-(bromomethylstyrene).

A commercial embodiment of the halogenated isobutylene-p-methylstyrene rubber ("BIMSM" rubber) of the present invention is EXXPRO™ elastomers (ExxonMobil Chemical Company, Houston, Tex.), having a Mooney viscosity (ML 1+8 at 125° C., ASTM D1646) of from 30 to 50, a p-methylstyrene content of from 5 to 7.5 wt % (measured prior to bromination of the copolymer), and a bromine content of from 0.45 to 2.2 mol % relative to the halogenated isobutylene-p-methylstyrene rubber.

The elastomer is present in the elastomeric composition in a range from up to 90 phr in one embodiment, and from up to 80 phr in another embodiment. Because of the need to control the leachables in the elastomeric composition, the inclusion of other elastomeric polymers, or secondary rubbers, is generally limited to not more than 20 phr, and in one embodiment, the amount of secondary rubber is limited to not more than 10 phr.

The elastomeric compositions include a variety of other components and are cured to form cured elastomeric compositions that ultimately are fabricated into the pharmaceutical stoppers and seals. For example, the elastomeric compositions may comprise: a) at least one filler, for example, calcium carbonate, clay, mica, silica, silicates, talc, titanium dioxide, starch, wood flour, carbon black, or mixtures thereof, and; b) at least one cure package or curative or wherein the composition has undergone at least one process to produce a cured composition.

Fillers

The elastomeric composition may have one or more filler components. Calcined clay is widely used as 'clean' filler, i.e., a filler that exhibits a low level of extractables and/or leachables, by the pharmaceutical industry. The fillers are typically present at a level of from 10 to 100 phr of the blend, more preferably from 30 to 80 phr in another embodiment, and from 50 to 80 phr in yet another embodiment.

Processing Oils and Aids

Due to the requirement of a 'clean' elastomer and the need to restrict potential leachables in the composition, the amount of additional conventional processing oils and aids, such as plastomers, is very limited. At most, if present, a processing oil or aid is present in an amount of not more than 10 phr. Preferably, paraffinic, naphthenic and/or aromatic oils, as well as plastomers and other processing oils, are substantially absent from the composition; meaning, they have not been deliberately added to the compositions, or, in the alternative, if present, are only present up to 0.2 wt % of the inventive compositions.

Crosslinking Agents, Curatives, Cure Packages, and Curing Processes

The elastomeric compositions and the articles made from those compositions may comprise or be manufactured with the aid of at least one cure package, at least one curative, at least one crosslinking agent, and/or undergo a process to cure the elastomeric composition. As used herein, at least one curative package refers to any material or method capable of imparting cured properties to a rubber as commonly understood in the industry.

One or more crosslinking agents are preferably used in the elastomeric compositions of the present invention. The absence of double bonds along the backbone of the elastomer and the presence of the alkylstyrene derived monomer pendant to the elastomer backbone, as well as the need in the pharmaceutical industry to limit leachables in the composition, are factors in selecting appropriate curing agents for the BIMSM.

Resin cure systems may also be used, with or without accelerators and/or activators. Accelerators serve to control the onset of and rate of vulcanization, and the number and type of crosslinks that are formed. Activators are chemicals that increase the rate of vulcanization. General classes of accelerators include amines, diamines, guanidines, thioureas, thiazoles, thiurams, sulfenamides, sulfenimides, thiocarbamates, xanthates, and the like.

Halogen-containing elastomers such as the halogenated poly(isobutylene-co-p-methylstyrene) may be crosslinked by their reaction with metal oxides. The metal oxide is thought to react with halogen groups in the polymer to produce an active intermediate which then reacts further to produce carbon-carbon bonds. Zinc halide is liberated as a by-product and it serves as an autocatalyst for this reaction. In particular, the following metal oxides are common curatives that will function in the present invention: $ZnO$, $CaO$, $MgO$, $Al_2O_3$, $CrO_3$, $FeO$, $Fe_2O_3$, and $NiO$. These metal oxides can be used alone or in conjunction with the corresponding metal fatty acid complex (e.g., zinc stearate, calcium stearate, etc.), or with the organic and fatty acids added alone, such as stearic acid or salicylic acid, an alkylperoxide compound, diamines or derivatives thereof.

Processing

Elastomer blends are typically melt mixes wherein mixing of the components may be carried out by combining the polymer components, filler and other additives in any suitable mixing device such as a two-roll open mill, Brabender™ internal mixer, Banbury™ internal mixer with tangential rotors, Krupp internal mixer with intermeshing rotors, or preferably a mixer/extruder, by techniques known in the art. Typically, from 70% to 100% of the elastomer is first mixed for 20 to 90 seconds, or until the temperature reaches from 40° C. to 75° C. Then, ¾ of the filler, and the remaining amount of elastomer, if any, is typically added to the mixer, and mixing continues until the temperature reaches from 90° C. to 150° C. Next, the remaining filler is added, as well as the processing oil and any other desired additives such as a colorant, and mixing continues until the temperature reaches from 140° C. to 190° C. The masterbatch mixture is then finished by sheeting on an open mill and allowed to cool, for example, to from 60° C. to 100° C. when the curatives are added.

The cure agents such as phenolic resins, sulfur, stearic acid, and zinc oxide, may be present from 0.1 to 10 phr.

After the composition has been prepared, pharmaceutical articles such as stoppers may be cut from cured sheets of elastomer, molded or compression molded to the desired shapes. If cut from cured sheets, slabs of the elastomer blend are first formed into sheets of the necessary thickness and then heated to the cure temperature; the cure temperature being dependent on the selective curing method. When molding or compression molding, uncured elastomer is injected into molds and then subjected to heat sufficient to create the necessary curing and cross-linking of the elastomeric material.

Either before or after the pharmaceutical articles have been formed, depending on how the articles have been formed, the elastomeric compound is subjected to gamma irradiation. The amount of irradiation is in the range of 25 to 40 KGray of gamma irradiation.

Examples

Four elastomeric compositions were prepared to show the effects of γ-irradiation. The compositions are set forth in Table 1 below; all components are expressed in parts per hundred (phr).

TABLE 1

| Phr | A | B | C | D |
|---|---|---|---|---|
| BIMSM[1] | 100 | | | |
| Bromobutyl[2] | | 100 | | |
| Chlorobutyl[3] | | | 100 | |
| Butyl[4] | | | | 100 |
| Calcined Clay | 80 | 80 | 80 | 80 |
| ZnO | 2 | 2 | 5 | 5 |
| Stearic Acid | 2 | | | 1 |
| Octylphenol-formaldehyde resin | 2 | 2 | 2 | 6 |
| Polychloroprene | | | | 5 |

[1]Mooney Viscosity of 35 ± 5 ML1 + 8 @125° C., 5 wt % PMS, 0.75 mol % bromine
[2]Mooney Viscosity of 32 ± 5 ML1 + 8 @125° C., 1.7 mol % isoprene, 2.10 wt % bromine
[3]Mooney Viscosity of 38 ± 5 ML1 + 8 @125° C., 1.95 mol % isoprene, 1.26 wt % chlorine
[4]Mooney Viscosity of 51 ± 5 ML1 + 8 @125° C., 1.7 mol % isoprene The four compounds were subjected to two different dosages of γ-irradiation, 25 KGray and 40 KGray, as well as oven aging each compound for 3 days at 121° C. The physical properties of the compounds were also tested prior to any pre-treatment. The results of the testing are set forth in Table 2 below.

TABLE 2

| Compound | Pre-treatment | 100% Modulus (MPa) | Tensile Strength (MPa) | Elongation to Break × 0.01 (%) | Shore A Hardness × 0.1 | Tear Strength (N/mm) | Compression Set |
|---|---|---|---|---|---|---|---|
| A | None | 1.18 | 3.39 | 6.1 | 4.5 | 15.25 | |
|   | 25K Gray | 1 | 3.74 | 6.5 | 3.9 | | |
|   | 40K Gray | 0.99 | 3.56 | 6.9 | 3.7 | | |
|   | Air oven aging | 1.78 | 2.9 | 3.6 | 5.2 | | |
| B | None | 1.2 | 5.79 | 6.5 | 4.2 | 18.29 | |
|   | 25K Gray | 1.68 | 2.6 | 3.2 | 4.6 | | |
|   | 40K Gray | 1.86 | 2.42 | 2.1 | 4.5 | | |
|   | Air oven aging | 1.69 | 2.78 | 4 | 4.6 | | |
| C | None | 1.32 | 3.52 | 4.7 | 4.4 | 16.28 | 24 |
|   | 25K Gray | 1.63 | 2.32 | 3.1 | 4.6 | | 26 |
|   | 40K Gray | 1.78 | 2.41 | 1.9 | 4.7 | | 27 |
|   | Air oven aging | 1.92 | 2.84 | 3 | 4.7 | | |
| D | None | 0.86 | n/a | n/a | 3.8 | 14.91 | 31 |
|   | 25K Gray | 0.58 | 3.79 | 7.7 | 2.8 | | 55 |
|   | 40K Gray | 0.42 | n/a | n/a | 2.3 | | 72 |
|   | Air oven aging | 1.49 | 4.93 | 5.3 | 4.5 | | |

When possible, standard ASTM tests were used to determine the cured compound physical properties (see Table 1). Stress/strain properties (tensile strength, elongation at break, modulus values) were measured at room temperature using an Instron 4202 or an Instron Series IX Automated Materials Testing System 6.03.08. Tensile measurements were done at ambient temperature on specimens (dog-bone shaped) width of 0.25 inches (0.62 cm), and a length of 1.0 inches (2.5 cm) length (between two tabs) were used. The thickness of the specimens varied and was measured manually by Mitutoyo Digimatic Indicator connected to the system computer. The specimens were pulled at a crosshead speed of 20 inches/min. (51 cm/min.) and the stress/strain data was recorded. The average stress/strain value of at least three specimens is reported. The error (2σ) in Tensile measurements is ±0.47 MPa units. The error (2σ) in measuring 100% Modulus is ±0.11 MPa units; the error (2σ) in measuring Elongation is ±13% units. Shore A hardness was measured at room temperature by using a Zwick Duromatic.

In comparing the change in tensile property and hardness of the four compounds upon γ-irradiation and air oven aging, it can be observed that compound A, comprising the BIMSM polymer, maintains its hardness, modulus, tensile and elongation to break properties to a significant degree after being subjected to 40 KGray γ-irradiation. On the other hand, compounds B and C, respectively containing the bromobutyl and chlorobutyl polymers, experience an increase in modulus and large reductions in both tensile strength and elongation to break. The physical property change upon 40 KGray γ-irradiation is similar or greater than air oven aging at 121° C. for 3 days for the halobutyl containing compounds B and C. For compound D, comprising the non-halogenated butyl polymer, a large reduction in modulus and hardness is observed resulting from chain scissoring during the γ-irradiation sterilization process.

It is also noted the compression set increases upon irradiation for compound D but not the chlorobutyl based compound C. Compression set values for compounds A and B were not obtainable due to difficulty in removing the compounds from the mold prior to testing.

When comparing the change in properties as a percentage change, it can be observed that the percentage change for the tensile properties of compound A upon 40 KGray γ-irradiation is less than 20% while that of compounds B through D is greater than 35%. It is also noted that the modulus of halobutyl compounds B and C increase upon γ-irradiation while that of regular butyl comprising compound D decreases. For the BIMSM based compound A, the modulus also decreases, though by a significantly smaller amount than for compound D. In reviewing the data of Table 2, it can be seen that the change trends for compound A go in the same direction as those of the non-halogenated butyl compound D and in the opposite direction for the chorobutyl and bromobutyl. Thus, the presence of the styrene pendant to the BIMSM polymer backbone, more than the presence of the halogen, mitigates the property changes of the material upon γ-irradiation. It is theorized that the benzene ring pendant to the polymer backbone acts as a free radical trap and prevents the polymer from chain scissoring. As the percentage of the alkyl-styrene derived units in the copolymer increases, the stability of the polymer when subjected to the gamma irradiation sterilization is expected. Thus, for use in applications wherein the elastomeric composition is to be subjected to such sterilization methods, for improved composition stability, wherein the composition and the articles formed from the composition retain at least 80% of its original properties, the polymer should be derived from at least 5 wt % alkyl-styrene, with the polymer in the composition containing at least 5 wt % alkyl-styrene. In another embodiment, the polymer should contain at least 7 wt % alkyl-styrene; and in yet another embodiment, the polymer should contain at least 8.5 wt % alkyl-styrene.

To determine if the observed superior γ-irradiation resistance of the BIMSM compound is dependent or not on the cure system, two other BIMSM containing compounds were prepared with other 'clean' cure system suitable for pharmaceutical stopper applications. These compositions are set forth in Table 3 below; the components are expressed in parts per hundred rubber (phr).

TABLE 3

|  | E | F |
|---|---|---|
| BIMSM | 100 | 100 |
| Calcined clay | 80 | 80 |
| Diamine carbamate | 0.75 |  |
| ZnO |  | 0.5 |
| Salicylic acid |  | 1 |

Compounds E and F were subjected to the gamma irradiation sterilization and physical property testing as compounds A through D above. The results are set forth in Table 4 below.

TABLE 4

| Compound | Pre-treatment | 100% Modulus (MPa) | Tensile Strength (MPa) | Elongation to Break × 0.01 (%) | Shore A Hardness × 0.1 | Tear Strength (N/mm) | Compression set (%) |
|---|---|---|---|---|---|---|---|
| E | None | 1.82 | 4.0 | 3.8 | 49 | 21.3 | 24 |
|  | 25K Gray | 1.73 | 3.5 | 4.0 | 44 |  | 26 |
|  | 40K Gray | 1.63 | 2.97 | 3.4 | 41 |  | 26 |
|  | Air oven aging | 2 | 4.05 | 3.6 | 47 |  |  |
| F | None | 2.83 | 4.91 | 2.7 | 53 | 22.55 | 12 |
|  | 25K Gray | 2.21 | 4.2 | 3.9 | 47 |  | 16 |
|  | 40K Gray | 2.24 | 4.04 | 3.4 | 44 |  | 19 |
|  | Air oven aging | 5.03 | 5.73 | 1.3 | 61 |  |  |

It can be observed that the diamines carbamate and salicylic acid cured BIMSM based compounds also exhibit relatively stable physical and compression set properties after being subjected to gamma irradiation. Thus, retention of the physical properties of the BIMSM based compound following gamma-irradiation are not based on the cure package; though it is evident that the cure package does affect the original properties of the compound.

Thus, the application discloses the following embodiments:

A. A method of producing elastomeric pharmaceutical articles, the method comprising the steps of a) preparing an elastomeric compound comprising a polymer prepared by reacting a mixture of i) a $C_4$ to $C_7$ isoolefin monomer, ii) a styrene based monomer, and optionally iii) a $C_4$ to $C_{14}$ multiolefin monomer wherein the polymer contains 5 to 15 wt % of styrene derived units, b) subjecting the elastomeric compound to gamma irradiation, and c) forming an article with the compound;

B. The method of producing the elastomeric pharmaceutical article of embodiment A, wherein after subjecting the elastomeric compound to gamma irradiation, tensile strength of the compound is changed by not more than twenty percent of the tensile strength of the compound prior to the gamma irradiation;

C. The method of producing the elastomeric pharmaceutical article of embodiment A or B, wherein after subjecting the elastomeric compound to gamma irradiation, the 100% modulus of the compound is changed by not more than twenty percent of the 100% modulus of the compound prior to the gamma irradiation;

D. The method of producing the elastomeric pharmaceutical article of any one or combination of embodiments A to C, wherein the elastomeric compound is further comprised of a cure package and at least one filler;

E. The method of producing the elastomeric pharmaceutical article of any one or combination of embodiments A to D, wherein the elastomeric compound is subjected to 25 to 40 KGray of gamma irradiation;

F. The method of producing the elastomeric pharmaceutical article of any one or combination of embodiments A to E, wherein the polymer is halogenated;

G. The method of producing the elastomeric pharmaceutical article of any one or combination of embodiments A to F, wherein the polymer is halogenated with either bromine or chlorine;

H. The method of producing the elastomeric pharmaceutical article of any one or combination of embodiments A to G, wherein the multiolefin is present in the reaction mixture in an amount of 15 to 0.5 wt %;

I. The method of producing the elastomeric pharmaceutical article of any one or combination of embodiments A to H, wherein the styrene based monomer is present in the reaction mixture in an amount of 10 to 7.5 wt %;

J. The method of producing the elastomeric pharmaceutical article of any one or combination of embodiments A to I, wherein the isoolefin is selected from the group consisting of isobutylene, 2-methyl-1-butene, 3-methyl-1-butene, 2-methyl-2-butene, 1-butene, 2-butene, hexene, and 4-methyl-1-pentene;

K. The method of producing the elastomeric pharmaceutical article of any one or combination of embodiments A to J, wherein the styrene monomer is selected from the group consisting of styrene, halostyrene, alkylstyrene, and haloalkylstyrene;

L. The method of producing the elastomeric pharmaceutical article of any one or combination of embodiments A to K, wherein the multiolefin is selected from the group consisting of isoprene, butadiene, 2,3-dimethyl-1,3-butadiene, myrcene, 6,6-dimethyl-fulvene, hexadiene, cyclopentadiene, and piperylene;

M. The method of producing the elastomeric pharmaceutical article of any one or combination of embodiments A to L, wherein the styrene monomer is a functionalized alkylstyrene;

N. The method of producing the elastomeric pharmaceutical article of any one or combination of embodiments A to M, wherein the articles are formed prior to subjecting the composition to the gamma irradiation;

O. The method of producing the elastomeric pharmaceutical article of any one or combination of embodiments A to N, wherein the article is a vial stopper or a vial seal;

P. A pharmaceutical article made by any one or any combination of embodiments A to N;

Q. An elastomeric pharmaceutical article, the article being comprised of a polymer, the polymer being a random polymer of i) $C_4$ to $C_7$ isoolefin derived units, ii) 5 to 15 wt % para-methylstyrene derived units, and optionally iii) a $C_4$ to $C_{14}$ multiolefin derived units, wherein the article is characterized by being subjected to at least 25 KGray of gamma irradiation and following irradiation the article retains at least 80% of its original tensile strength and 100% modulus;

R. The elastomeric pharmaceutical article of embodiment Q, wherein the elastomeric compound is further comprised of a cure package and at least one filler;

S. The elastomeric pharmaceutical article of embodiment Q or R, wherein the elastomeric compound is subjected to 25 to 40 KGray of gamma irradiation;

T. The elastomeric pharmaceutical article of any one or combination of embodiments Q to S, wherein the polymer is halogenated;

U. The elastomeric pharmaceutical article of any one or combination of embodiments Q to T, wherein the polymer is halogenated with either bromine or chlorine;

V. The elastomeric pharmaceutical article of any one or combination of embodiments Q to U, wherein the multiolefin is present in the polymer in an amount of 15 to 0.5 wt %;

W. The elastomeric pharmaceutical article of any one or combination of embodiments Q to V, wherein the styrene based monomer is present in an amount of 10 to 7.5 wt %;

X. The elastomeric pharmaceutical article of any one or combination of embodiments Q to W, wherein the isoolefin is selected from the group consisting of isobutylene, 2-methyl-1-butene, 3-methyl-1-butene, 2-methyl-2-butene, 1-butene, 2-butene, hexene, and 4-methyl-1-pentene; and Y. The elastomeric pharmaceutical article of any one or combination of embodiments Q to X, wherein the multiolefin is selected from the group consisting of isoprene, butadiene, 2,3-dimethyl-1,3-butadiene, myrcene, 6,6-dimethyl-fulvene, hexadiene, cyclopentadiene, and piperylene.

What is claimed is:

1. A method of producing elastomeric pharmaceutical articles, the method comprising the four steps of:
    a) preparing an elastomeric compound comprising a functionalized polymer prepared by reacting a mixture of i) isobutylene, ii) an alkyl-styrene based monomer, and optionally iii) a $C_4$ to $C_{14}$ multiolefin monomer wherein the polymer contains 5 to 15 wt % of alkyl-styrene derived units, 0.1 to 10 wt % of a halogen, and the alkyl-styrene derived units are functionalized only by the halogen, wherein the elastomeric compound is further comprised of at least one filler and a cure package comprising at least one component selected from the group consisting of a phenolic resin, a metal oxide, sulfur, and stearic acid,
    b) curing the elastomeric compound,
    c) subjecting the elastomeric compound to gamma irradiation, and
    d) forming an article with the compound,
    wherein after subjecting the elastomeric compound to the gamma irradiation, either the tensile strength or the 100% modulus of the compound is changed by not more than twenty percent of the compound prior to the gamma irradiation.

2. The method of producing the elastomeric pharmaceutical article of claim 1, wherein after subjecting the elastomeric compound to gamma irradiation, tensile strength of the compound is changed by not more than twenty percent of the tensile strength of the compound prior to the gamma irradiation.

3. The method of producing the elastomeric pharmaceutical article of claim 1, wherein after subjecting the elastomeric compound to gamma irradiation, the 100% modulus of the compound is changed by not more than twenty percent of the 100% modulus of the compound prior to the gamma irradiation.

4. The method of producing the elastomeric pharmaceutical article of claim 1, wherein the elastomeric compound is subjected to 25 to 40 KGray of gamma irradiation.

5. The method of producing the elastomeric pharmaceutical article of claim 1, wherein the polymer is halogenated with either bromine or chlorine.

6. The method of producing the elastomeric pharmaceutical article of claim 1, wherein the multiolefin is present in the reaction mixture in an amount of 15 to 0.5 wt %.

7. The method of producing the elastomeric pharmaceutical article of claim 1, wherein the alkyl-styrene based monomer is present in the reaction mixture in an amount of 10 to 7.5 wt %.

8. The method of producing the elastomeric pharmaceutical article of claim 1, wherein the articles are formed prior to subjecting the composition to the gamma irradiation.

9. The method of producing the elastomeric pharmaceutical article of claim 1, wherein the article is a vial stopper or a vial seal.

* * * * *